(12) United States Patent
Scifert et al.

(10) Patent No.: US 7,513,901 B2
(45) Date of Patent: Apr. 7, 2009

(54) GRAFT SYRINGE ASSEMBLY

(75) Inventors: Jeffrey L. Scifert, Arlington, TN (US); Stephen A. Mariano, Westford, MA (US); Richard Stephen Wisdom, Mattapan, MA (US); Gary Robert Whipple, Attleboro, MA (US); A. David Boccuti, Arlington, MA (US); Roger J. White, Arlington, MA (US); Thomas T. Washburn, Groton, MA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 561 days.

(21) Appl. No.: 11/132,268

(22) Filed: May 19, 2005

(65) Prior Publication Data

US 2006/0264964 A1 Nov. 23, 2006

(51) Int. Cl.
*A61B 17/58* (2006.01)
(52) U.S. Cl. .......................... 606/93; 606/92
(58) Field of Classification Search .......... 606/92–95; 604/187, 218, 239, 241, 188, 240, 533–535; 433/89–90
See application file for complete search history.

(56) References Cited

U.S. PATENT DOCUMENTS

| | | | |
|---|---|---|---|
| 4,340,148 A * | 7/1982 | Beckham | 215/329 |
| 4,384,581 A * | 5/1983 | Conway | 604/207 |
| 4,576,152 A | 3/1986 | Müller et al. | |
| 4,592,728 A * | 6/1986 | Davis | 435/80 |
| 4,645,488 A | 2/1987 | Matukas | |
| 4,655,747 A | 4/1987 | Allen, Jr. | |
| 4,687,472 A | 8/1987 | Gross | |
| 4,751,921 A | 6/1988 | Park | |
| 4,784,607 A * | 11/1988 | Francois | 433/90 |
| 4,834,714 A | 5/1989 | Lascar et al. | |
| D306,069 S | 2/1990 | Kelly et al. | |
| 4,925,449 A | 5/1990 | Saez et al. | |
| 4,929,238 A | 5/1990 | Baum | |
| D312,873 S | 12/1990 | Bradrick et al. | |
| D315,407 S | 3/1991 | Bradrick et al. | |
| 5,002,538 A * | 3/1991 | Johnson | 604/240 |
| D320,276 S | 9/1991 | Baum | |
| D321,053 S | 10/1991 | Baum | |
| 5,071,040 A | 12/1991 | Laptewicz, Jr. | |
| D325,437 S | 4/1992 | Hull | |
| 5,129,888 A | 7/1992 | Bidoia | |
| 5,246,011 A | 9/1993 | Caillouette | |
| 5,290,259 A * | 3/1994 | Fischer | 604/218 |
| 5,304,128 A * | 4/1994 | Haber et al. | 604/68 |
| 5,306,258 A | 4/1994 | de la Fuente | |
| 5,352,410 A * | 10/1994 | Hansen et al. | 422/58 |

(Continued)

*Primary Examiner*—Eduardo C Robert
*Assistant Examiner*—Julianna N Harvey
(74) *Attorney, Agent, or Firm*—Kalow Springut

(57) ABSTRACT

The invention relates, according to one embodiment, to a graft syringe assembly for delivering bone graft material is disclosed. The graft syringe assembly comprises a syringe subassembly including a syringe barrel having an inner chamber adapted for receiving bone graft material, a plunger adapted for expelling bone graft material from the inner chamber, the plunger slidably received within the inner chamber, and a syringe adapter coupled to the syringe barrel. The graft syringe assembly further comprises a connection subassembly coupled to the syringe adapter, and a delivery tube subassembly coupled to the connection subassembly, wherein the connection subassembly is configured to allow the delivery tube subassembly to rotate relative to the syringe subassembly.

20 Claims, 12 Drawing Sheets

U.S. PATENT DOCUMENTS

| | | | |
|---|---|---|---|
| 5,409,465 A | 4/1995 | Boggs et al. | |
| 5,496,284 A | 3/1996 | Waldenburg | |
| 5,558,136 A | 9/1996 | Orrico | |
| 5,561,372 A | 10/1996 | Watanabe et al. | |
| 5,605,541 A | 2/1997 | Holm | |
| D385,627 S | 10/1997 | Cook et al. | |
| 5,681,317 A | 10/1997 | Caldarise | |
| 5,814,022 A | 9/1998 | Antanavich et al. | |
| 5,842,786 A | 12/1998 | Solomon | |
| 6,017,349 A | 1/2000 | Heller et al. | |
| 6,048,346 A | 4/2000 | Reiley et al. | |
| 6,086,569 A | 7/2000 | Schweizer | |
| 6,142,998 A | 11/2000 | Smith et al. | |
| 6,217,338 B1 | 4/2001 | Tieman | |
| 6,312,258 B1 * | 11/2001 | Ashman | 433/172 |
| 6,367,962 B1 | 4/2002 | Mizutani et al. | |
| 6,375,659 B1 | 4/2002 | Erbe et al. | |
| 6,613,018 B2 | 9/2003 | Bagga et al. | |
| 6,644,309 B2 | 11/2003 | Casper et al. | |
| 6,645,213 B2 | 11/2003 | Sand et al. | |
| 6,723,131 B2 * | 4/2004 | Muschler | 623/23.51 |
| 2002/0049448 A1 | 4/2002 | Sand et al. | |
| 2002/0082605 A1 | 6/2002 | Reiley et al. | |
| 2002/0087125 A1 | 7/2002 | Pokorney | |
| 2003/0069545 A1 | 4/2003 | Arm | |
| 2004/0024409 A1 * | 2/2004 | Sand et al. | 606/92 |
| 2004/0167562 A1 | 8/2004 | Osorio et al. | |
| 2004/0204715 A1 | 10/2004 | Evans et al. | |
| 2005/0124997 A1 | 6/2005 | Pajunk et al. | |

\* cited by examiner

GRAFT SYRINGE ASSEMBLY

BACKGROUND OF THE INVENTION

The invention relates generally to a graft syringe assembly, and method of using same, for the delivery of bone graft material to treat a surgical site.

In the surgical field, it is not uncommon for surgeons to provide bone graft material to anatomical structures affected during surgical procedures to aid in the bone regeneration process and to promote healing. Unfortunately, the current state of the art for devices designed for delivering such material suffer from many disadvantages. These disadvantages include not being able to mix bone graft material and other fluids in the device, not offering flexibility with the delivery point of bone graft material once the device is inside the patient's body where movement is limited, not being able to fit fixtures of varying size and shape for delivering different amounts of bone graft material, not providing a visual indicator of the amount of bone graft material being delivered, not providing a visual indicator of the amount of fluid that is mixed in the syringe device.

Accordingly, the invention provides various embodiments of devices, methods of use, and kits, for the delivery of bone graft material to treat affected anatomical sites, that overcome the disadvantages of known devices and methods while offering features not present in known art. Although certain deficiencies in the related art are described in this background discussion and elsewhere, it will be understood that these deficiencies were not necessarily heretofore recognized or known as deficiencies. Furthermore, it will be understood that, to the extent that one or more of the deficiencies described herein may be found in an embodiment of the claimed invention, the presence of such deficiencies does not detract from the novelty or non-obviousness of the invention or remove the embodiment from the scope of the claimed invention.

SUMMARY OF THE INVENTION

The invention, according to one embodiment, relates to a graft syringe assembly for delivering bone graft material is disclosed. The graft syringe assembly comprises a syringe subassembly including a syringe barrel having an inner chamber adapted for receiving bone graft material, a plunger adapted for expelling bone graft material from the inner chamber, the plunger slidably received within the inner chamber, and a syringe adapter coupled to the syringe barrel. The graft syringe assembly further comprises a connection subassembly coupled to the syringe adapter, and a delivery tube subassembly coupled to the connection subassembly, wherein the connection subassembly is configured to allow the delivery tube subassembly to rotate relative to the syringe subassembly.

The invention, according to another embodiment, relates to a graft syringe assembly for delivering bone graft material is disclosed. The graft syringe assembly comprises a syringe subassembly including a syringe barrel having a proximal end, a distal end, and an inner chamber adapted for receiving bone graft material, the inner chamber having a proximal opening and a distal opening, a plunger adapted for expelling bone graft material through the distal opening of the inner chamber, the plunger slidably received within the inner chamber through the proximal opening, and a syringe adapter coupled to the distal end of the syringe barrel. The graft syringe assembly further comprises a connection subassembly coupled to the syringe adapter, and a delivery tube subassembly coupled to the connection subassembly, wherein the connection subassembly is configured to allow the delivery tube subassembly to rotate relative to the syringe subassembly.

The invention, according to another embodiment, relates to a kit for delivering bone graft material is disclosed. The kit comprises bone graft material, a syringe subassembly including a syringe barrel having an inner chamber adapted for receiving the bone graft material, a plunger adapted for expelling bone graft material from the inner chamber, the plunger slidably received within the inner chamber, and a syringe adapter coupled to the barrel. The kit further comprises a first connection subassembly adapted for coupling to the syringe adapter, a second connection subassembly adapted for coupling to the syringe adapter, a third connection subassembly adapted for coupling to the syringe adapter, and a delivery tube subassembly adapted for coupling to the first connection subassembly, wherein the first connection subassembly is configured to allow the delivery tube subassembly to rotate relative to the syringe subassembly.

BRIEF DESCRIPTION OF THE DRAWINGS

The present invention can be more fully understood by reading the following detailed description of the presently preferred embodiments together with the accompanying drawings, in which like reference indicators are used to designate like elements, and in which.

DETAILED DESCRIPTION OF PREFERRED EMBODIMENTS

The present invention provides various embodiments of graft syringe assemblies for delivering bone graft material to anatomical structures affected during surgical procedures to aid in the bone regeneration process, method of using the same, and kits for same.

As used herein, "bone graft material" refers to, for example, autogenous morselized bone graft, autogenous bone graft strips, allograft chips, demineralized bone matrix in putty, gel, strip, or other forms, xenografts and fired bone, bone graft substitutes, such as hydroxyapatite, calcium carbonate, beta tricalcium phosphate, calcium sulfate or mineralized collagen, collagen-ceramic mixtures, natural or synthetic polymers, such as collagen particles, meshes, sponges, and gels, hyaluronic acid and derivatives thereof, liposomes or other natural biomaterials known as potential implants, or carriers of therapeutic agents, such as cytokines, growth factors, cells, antibiotics, analgesics, chemotherapeutic drugs, and the like, synthetic polymers, such as alpha-hydroxy polyesters, including polylactic acid, polyglycolic acid and their copolymers, polydioxanone, as well as poly methyl methacrylate, separately, in mixture or in admixture with any therapeutic agents, and bone graft replacements, such as recombinant bone morphogenetic proteins. In at least one embodiment, bone graft material includes granules sold under the tradename MasterGraft™.

Figure 1A:
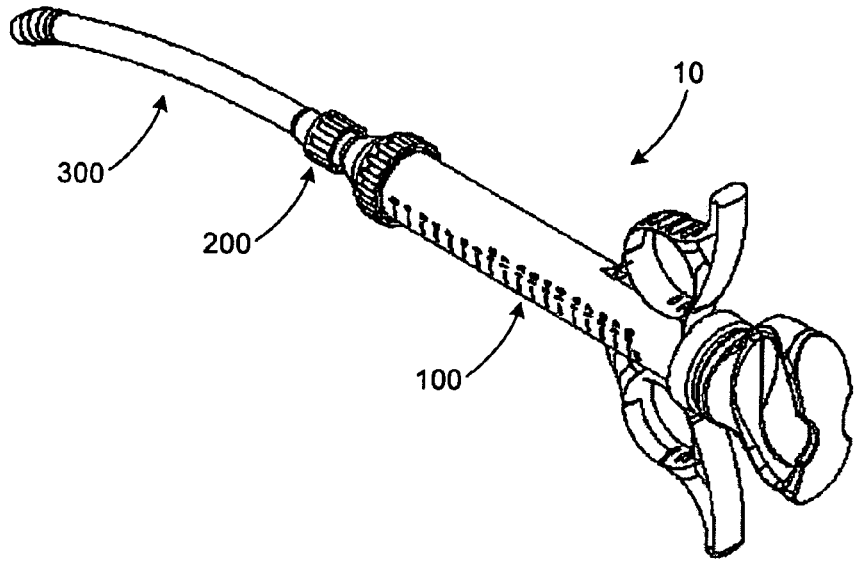
FIGS. 1a and 1b (exploded view) are perspective views of an illustrative graft syringe assembly in accordance with one embodiment of the invention.

FIG. 1a is a perspective view of an illustrative graft syringe assembly in accordance with one embodiment of the invention. As shown in FIG. 1a, graft syringe assembly 10 includes the syringe subassembly 100, the connection subassembly 200, and the delivery tube subassembly 300. Graft syringe assembly 10 is designed such that a surgeon may use the device to deliver bone graft material to affected surgical sites to aid in the bone regeneration process. Syringe subassembly 100 is configured to receive intraoperatively or maintain a pre-packaged bone graft material, and eventually, expel the bone graft material through the delivery tube subassembly 300 to the affected surgical site. The connection subassembly 200 serves as a connection point between the syringe subassembly 100 and delivery tube subassembly 300. Connection subassembly 200 is further adapted to allow the surgeon to freely rotate the delivery tube subassembly 300 relative to the syringe subassembly 100 to provide for more accurate delivery of the bone graft material. As described in more detail below, various connection subassemblies (including varying adapters and connectors) serving varying functions, and allowing for the attachment of additional medical components, may be employed with the graft syringe assembly of the invention.

Figure 1B:
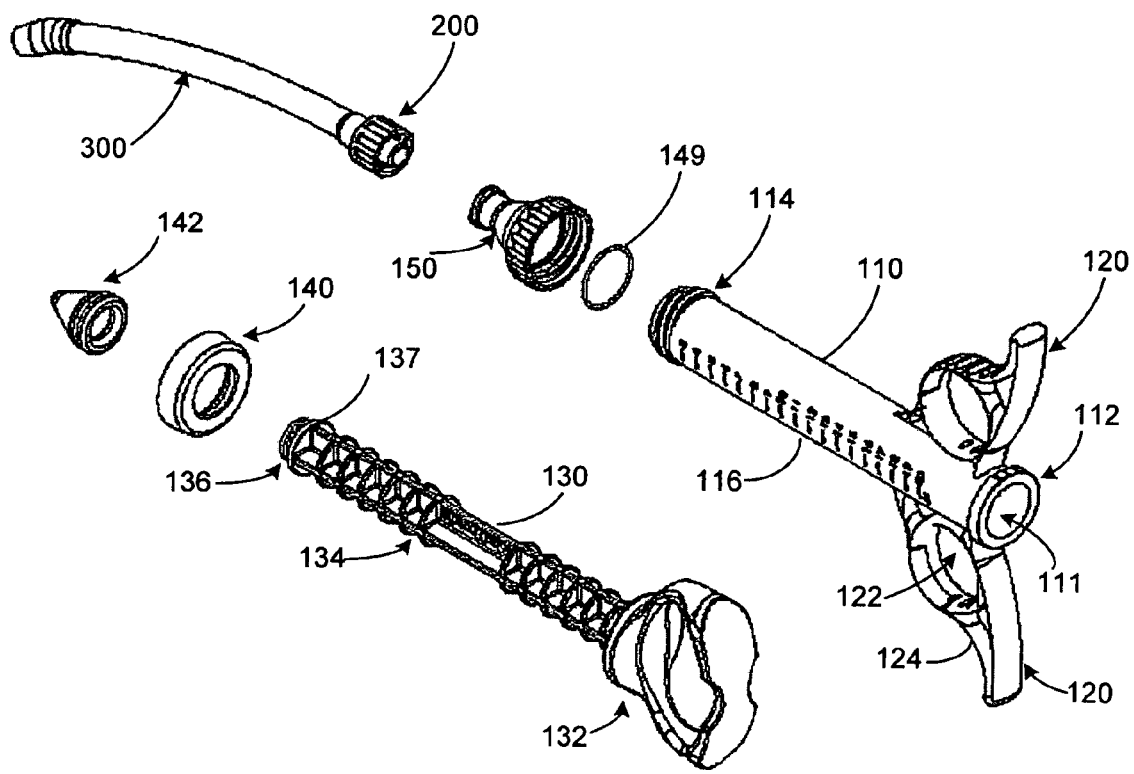

As shown in FIGS. 1a and 1b, syringe subassembly 100 is comprised of syringe barrel 110, syringe plunger 130, plunger locker ring 140, plunger seal 142, o-ring seal 149 and syringe adapter 150. Syringe barrel 110 is an elongated tubular member having a proximal end 112, a distal end 114, and an inner chamber 111. Volume graduations 116 are provided on the outside of syringe barrel 110 to aid the surgeon in determining the volume of bone graft material and contents contained in the syringe barrel 110. A pair of opposing finger grips 120 are defined on the outside of syringe barrel 110 for the surgeon to grip while depressing syringe plunger 130 in use of the graft syringe 10. As shown in FIGS. 1a and 1b, finger grips 120 are generally winged shaped, and each include a suitably configured bore 122 for receiving one of the user's fingers. Each finger grip 120 also has an outermost finger portion 124 suitably configured in a generally arcuate shape to provide yet another surface against which the surgeon can apply force with his fingers while depressing the plunger 130.

Figure 2:
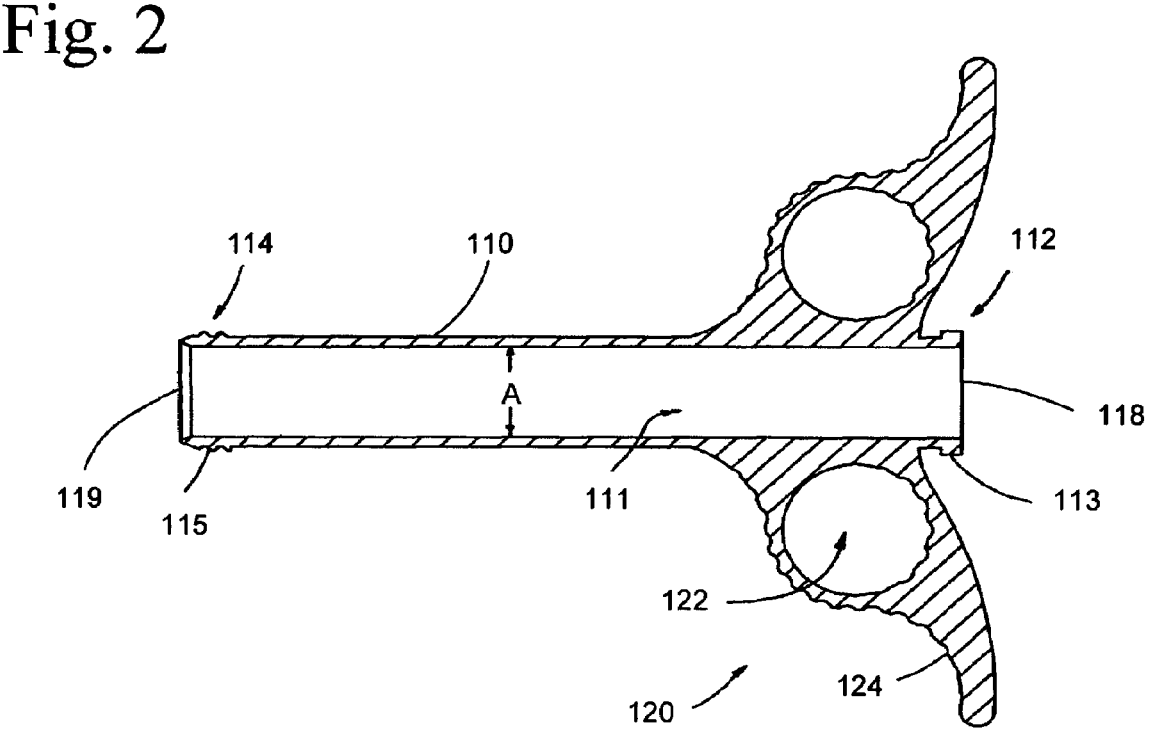
FIG. 2 is a side sectional view of the syringe barrel of FIGS. 1a and 1b in further detail in accordance with one embodiment of the invention.

FIG. 2 is a side sectional view of the syringe barrel of FIGS. 1a and 1b in further detail. As shown in FIG. 2, syringe barrel 110 includes external threads 115 on its distal end 114, and fitting 113 on its proximal end 112. External threads 115 are adapted for engaging the inner threads of the syringe adapter 150, described in more detail below with reference to FIGS. 3a, 3b, 3c. Fitting 113 is adapted to engage plunger lock ring 140 when the proximal end 112 of barrel 110 is sealed. In some embodiments, a plunger lock ring seal may be disposed between fitting 113 and plunger lock ring 140 to enhance the seal at the proximal end 112. Inner chamber 111 is defined by a generally axial bore extending through the body of syringe barrel 110 that terminates at a proximal opening 118 at proximal end 112, and distal opening 119 at distal end 114. Inner chamber 111 has an inner diameter A that remains substantially uniform over the length of the body of syringe barrel 110. Inner chamber 111 is also configured to slidably receive syringe plunger 130 and plunger seal 142. In some embodiments, syringe barrel 110 is constructed of transparent material to allow the bone graft material and the other contents within inner chamber 111 to be visible from outside the barrel 110.

Figure 12:
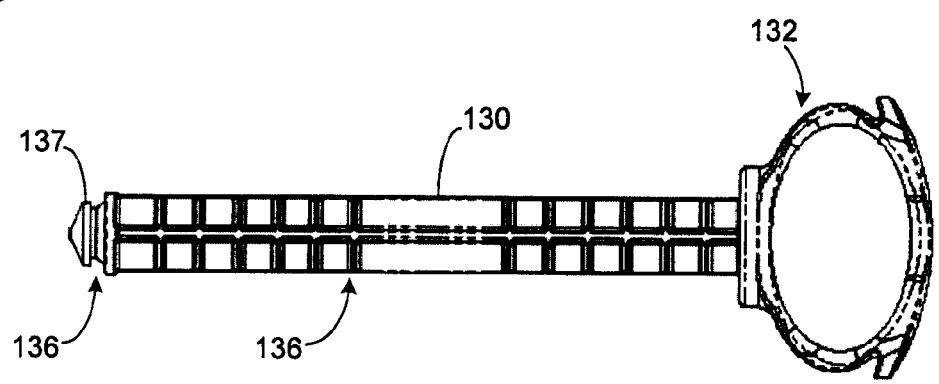
FIG. 12 is a side view of the plunger of FIG. 11 in further detail in accordance with one embodiment of the invention.

Returning to FIG. 1b, syringe plunger 130 is a generally elongate member having a proximal portion 132, body portion 134 and distal portion 136, as shown in side view in FIG. 12. As shown, the body portion 134 has a generally X-shaped cross-section with a plurality of disc-shaped axial supports disposed along its length. In alternate embodiments, body portion 134 may be provided in other cross-sectional shapes, for example, a solid cylindrical shapes. To aid the surgeon in depressing plunger 130, proximal portion 132 includes an oval-shaped grip ring 133 for improved gripping and to allow the surgeon to provide greater force to expel the bone graft material from inner chamber 111.

Figure 11:
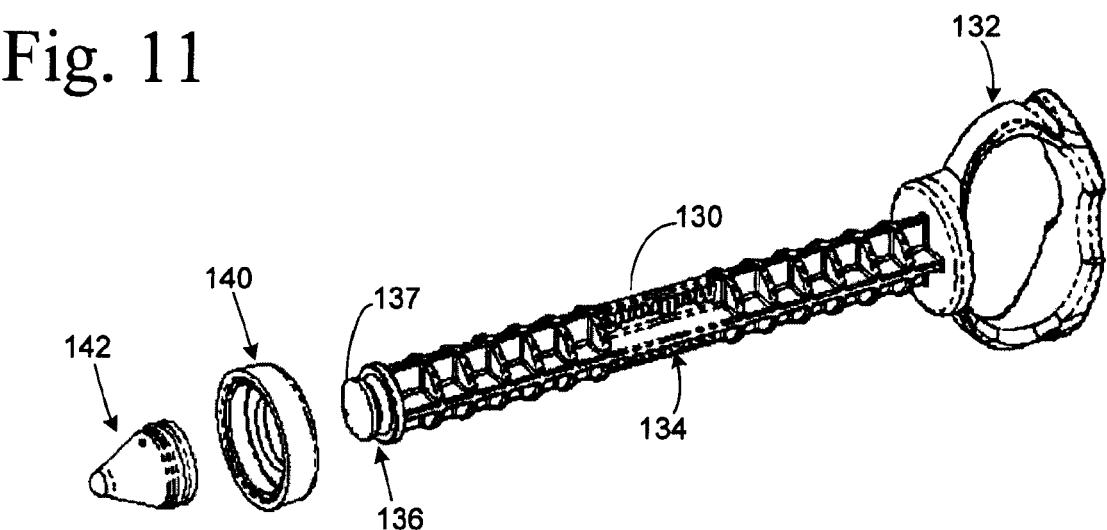
FIG. 11 is a perspective view of the plunger, plunger lock ring, and plunger seal of FIG. 1b in further detail in accordance with one embodiment of the invention.
Figure 13A:
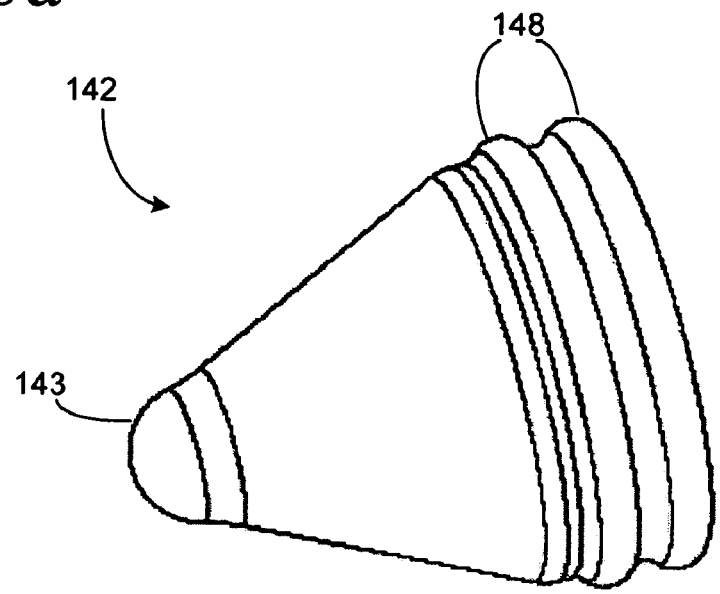
FIGS. 13a and 13b are perspective and side sectional views of the plunger seal of FIG. 11 in further detail in accordance with one embodiment of the invention.
Figure 13B:
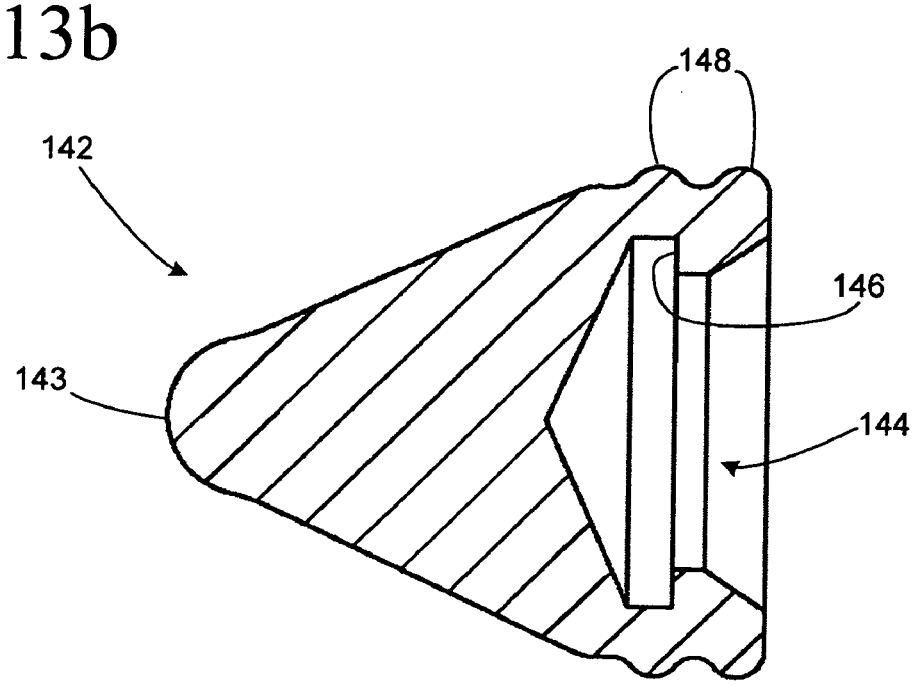

Another perspective exploded view of plunger 130, plunger lock ring 140 and plunger seal 142 in further detail is provided in FIG. 11. FIGS. 13a and 13b illustrate perspective and side sectional views of plunger seal 142 in further detail. In these embodiments, plunger seal 142 has a cavity 144 formed in its proximal end that is configured to engage the distal end 137 of plunger 130. Plunger seal 142 is removably attached to the distal end 137 of distal portion 136. Shoulder 146 secures seal 142 on distal end 137 for removeable attachment. Plunger seal 142 further includes a nose portion 143 and a plurality of peripheral ridges at its proximal end that are adapted to engage the inner diameter A of the inner chamber 111.

Syringe plunger 130 and plunger seal 142 are designed to be slidably inserted into inner chamber 111 of barrel 110, as shown assembled in FIG. 1a. When in use, plunger 130 and plunger seal 142 are adapted to expel the contents of the inner chamber 111 when depressed by the surgeon. Plunger seal 142 is sized to allow the plunger 130 to slide within inner chamber 111, but when plunger 130 and seal 142 are being used to expel bone graft material, seal 142 ensures that the contents are forced out, and prevents the contents or other fluids from passing the seal 142 as it slides forward.

As assembled in FIG. 1a, syringe plunger 130 is slidably fitted through plunger lock ring 140 such that distal portion 136 is disposed within inner chamber 111 of barrel 110, and proximal portion 132 is outside barrel 110. Plunger lock ring 140 is engagedly fitted to the proximal end 112 of barrel 110. In some embodiments, a plunger lock ring seal (not illustrated) is disposed between plunger lock ring 140 and proximal end 112, and compressed to provide a watertight seal. Plunger lock ring 140 restricts the sliding movement of distal portion 136 of plunger 130 within the inner chamber 111. Thus, plunger 130, plunger lock ring 140, the plunger lock ring seal, and fitting 113 each cooperate to seal proximal opening 118 of inner chamber 111.

When distributed, graft syringe assembly 10 may be supplied with bone graft material (not illustrated) already stored within the inner chamber 111. In a preferred embodiment, inner chamber 111 may be partially filled with bone graft material, such as ceramic granules sold under the tradename MasterGraft™. It should be appreciated, however, that any type of bone graft material, or compatible mixtures thereof, described above may also be employed.

In operation, when the surgeon applies force to the proximal portion 132 to depress the plunger 130, plunger seal 142 forces the bone graft material (and other contents) from the inner chamber 111 out distal opening 119 through adapter 150 to connection subassembly 200 to the delivery tube subassembly 300 and, finally, to the surgical site. Seal 142 is designed to expel all of the contents in the inner chamber 111, without letting any pass behind it as it depresses. To facilitate movement of the bone graft material through the delivery tube subassembly 300, blood or other fluid may be introduced to the bone graft material within inner chamber 111. This includes the addition and/or mixing of a liquid, gel, or fluid substance to the inner chamber 111 of the barrel 110 either before or after the addition of the bone graft material. This fluid may be introduced by needle or other device through an opening in the syringe adapter 150, or through an alternate side port provided on the barrel 110. Likewise, the syringe subassembly 100 can be used to accept a gel or other fluid through the distal opening 119 or the syringe adapter 150.

The various fluids that may be added to the inner chamber 111 include sterile water, saline, blood, or blood components including plasma, platelet-rich plasma, buffy coat, autologous growth factors or other concentrated blood components, red blood cells, white blood cells or platelets in any combination, as well as cryoprecipitates. Other suitable and intended fluids include bone marrow, as well as growth factor solutions suspensions or gels, which include any of the well known growth factors, such as Platelet-Derived Growth Factor (PDGF), Transforming Growth Factor Beta (TGF-beta.), Insulin-Like Growth Factor (IGF), Fibroblast Growth Factor (FGF), Epidermal Growth Factor (EGF), Vascular Endothelial Growth Factor (VEGF), Bone Morphogenetic Proteins (BMPs), and vectors for gene therapy. Further, cellular solutions, suspensions, and materials including osteoblasts, osteoprogenitor cells, chondroblasts, stem cells, or fibroblasts may also be used, as well as solutions or suspensions containing other therapeutic agents such as antibiotics, analgesics, antithrombinolytics, or chemotherapeutic agents. Further, bone graft replacements, such as recombinant bone morphogenetic proteins, may be added.

As shown in FIG. 1a, syringe adapter 150 is engagedly coupled to the distal end of 114 of barrel 110. An o-ring seal 149 is disposed between the barrel 110 and adapter 150, as shown in exploded view in FIG. 1b, to prevent fluid leakage during pressurization of the syringe barrel 110. Adapter 150 provides the added functionality of allowing several different types of devices/components to be in communication with the inner chamber 111 of barrel 110. In FIGS. 1a and 1b, connection subassembly 200 is engagedly coupled to the large bore luer lock connector of adapter 150, as well as delivery tube subassembly 300 to the syringe subassembly 100 and allows for fluid communication between these two important components. The fluid pathway from distal opening 119 of inner chamber 111 begins with adapter 150. In this embodiment, connection subassembly 200 is comprised of rotating septum cap 210 that is adapted for receiving one end of the delivery tube subassembly 300, and also attaching to syringe adapter 150.

Figure 3A:
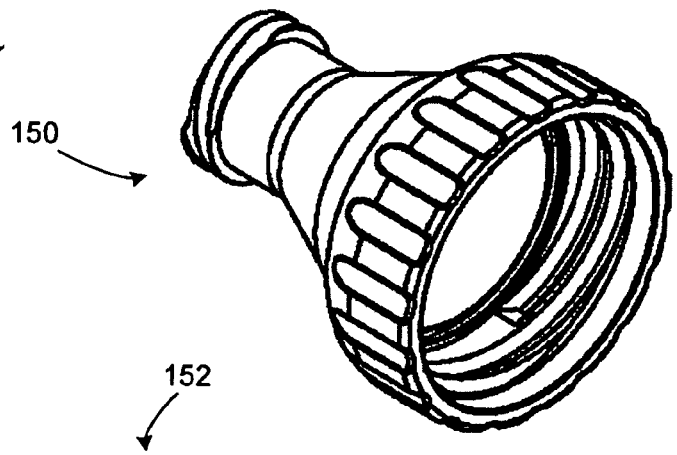
FIGS. 3a, 3b and 3c are perspective, side and side sectional views of the syringe adapter of FIGS. 1a and 1b in further detail in accordance with one embodiment of the invention.
Figure 3B:
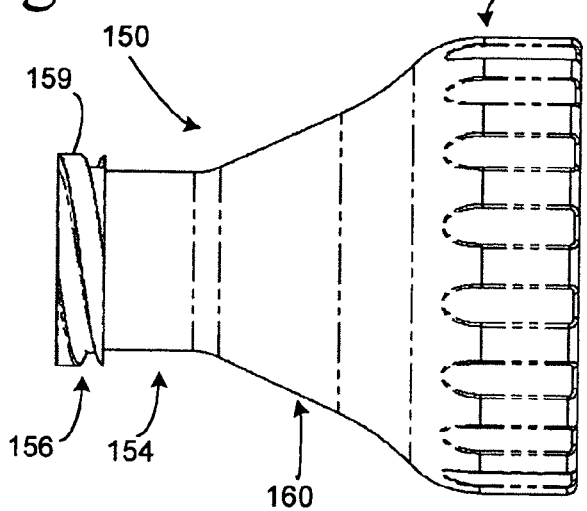
Figure 3C:
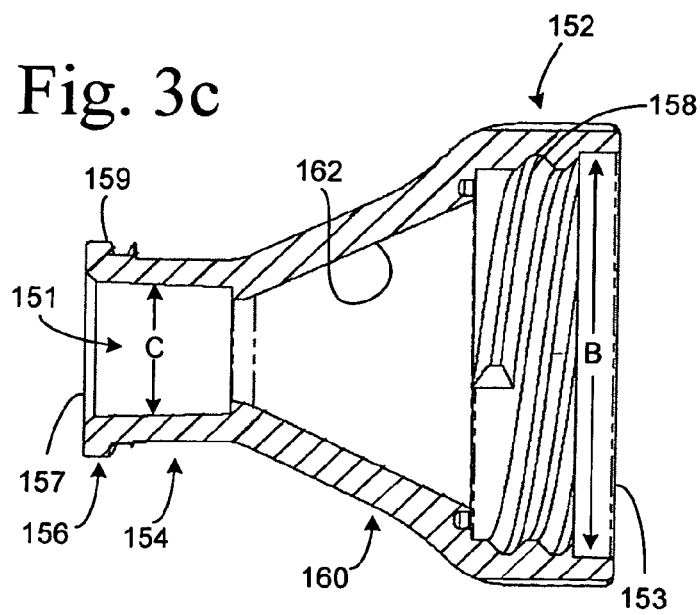

FIGS. 3a, 3b and 3c are perspective, side and side sectional views of the syringe cap of FIGS. 1a and 1b in further detail. Syringe adapter 150 is a generally tubular connector that is defined by its larger diameter proximal portion 152, conical body portion 160, neck portion 154 and smaller diameter distal portion 156. A bore 151 is formed through syringe adapter 150 that extends from proximal opening 153 through conical section 162 to distal opening 157, and vice versa. Bore 151 has a first inner diameter B in the proximal portion 152 that is generally narrowed through conical section 162 to the second inner diameter C in neck portion 154 and distal portion 156. The first inner diameter B is configured to receive the distal end 114 of barrel 110 through proximal opening 153, wherein inner threads 158 engage, or mate, with the external threads 115 located on the distal end 114. In some embodiments, conical section 162 is shaped to match and receive the shaped nose portion of plunger seal 142 so that the bone graft material is expelled from the adapter 150. The distal portion 156 includes external threads 159 for engaging connection subassembly 200.

Figure 4B:
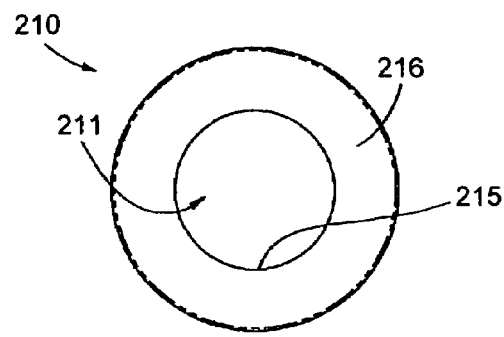
FIGS. 4a, 4b and 4c are perspective, front and side sectional views of the rotating septum cap of FIGS. 1a and 1b in further detail in accordance with one embodiment of the invention.
Figure 4A:
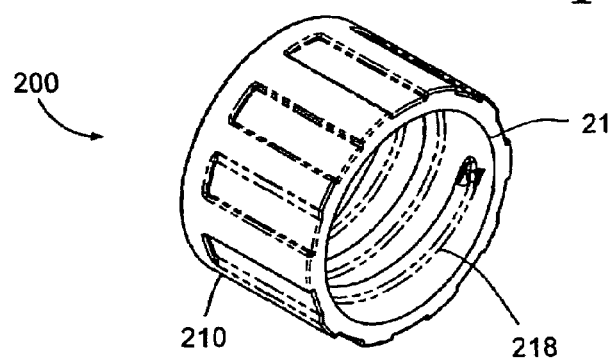
Figure 4C:
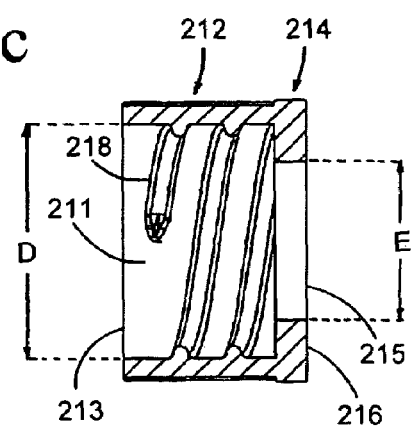

FIGS. 4a, 4b and 4c are perspective, front and side sectional views of the connection subassembly of FIGS. 1a and 1b in further detail. In this embodiment, connection subassembly 200 is comprised of rotating septum cap 210 that is adapted for receiving one end of the delivery tube subassembly 300, and also attaching to syringe adapter 150. Rotating septum cap 210 essentially functions as a luer lock, or locking nut, for receiving the luer fitting of delivery tube subassembly 300, and engagedly coupling to the syringe adapter 150. Rotating septum cap 210 is also a generally tubular connector that is generally defined by its two portions, proximal portion 212 and distal portion 214, and inner cavity 211 having proximal opening 213 with first inner diameter D and distal opening 215 with second inner diameter E. The inner face of the proximal portion 212 includes inner threads 218 for engaging, or mating, with the external threads 159 located on the distal portion 156 of syringe cap 150. The distal portion 214 also includes front face 216.

Figure 5:
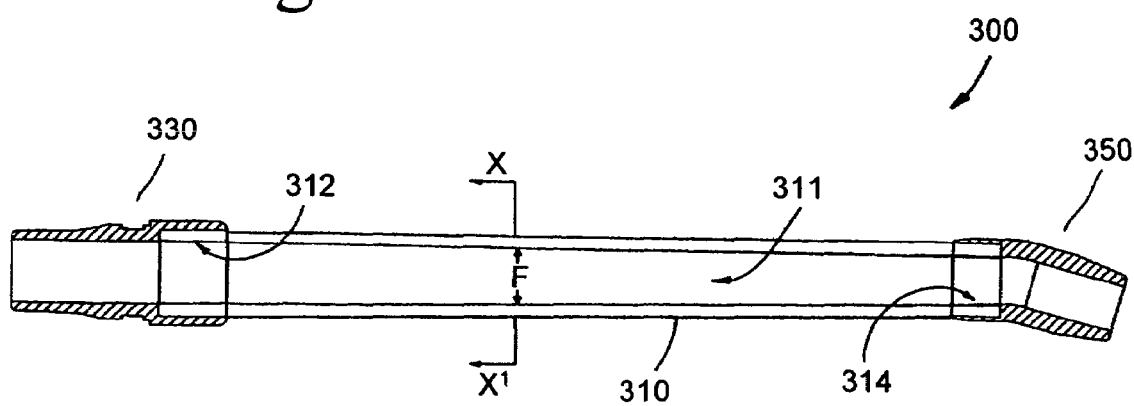
FIG. 5 is a side sectional view of the delivery tube subassembly of FIGS. 1a and 1b in further detail in accordance with one embodiment of the invention.

FIG. 5 is a side sectional view of the delivery tube subassembly of FIGS. 1a and 1b in further detail. Delivery tube subassembly 300 includes flexible delivery tube 310 having a delivery tip 350 affixed at one end, and a luer fitting 330 affixed to the opposing end. Delivery tube 310 has a passageway 311 with inner diameter F forced through it. In the embodiment of FIG. 5, the two opposing ends of delivery tube 310 are generally referred to as proximal portion 312 and distal portion 314. The luer fitting 330 is attached to the proximal portion 312, while the delivery tip 350 is attached to distal portion 314.

Figure 6:
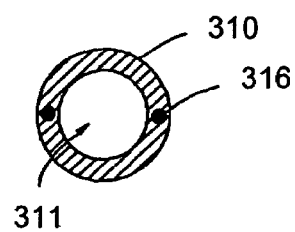
FIG. 6 is a front sectional view of the delivery tube of FIG. 5 in further detail in accordance with one embodiment of the invention.

Delivery tube 310 may further include wire members 316 disposed longitudinally in the walls of the tube 310, as shown in FIG. 6, to provide adjustability (and rigidity) in the delivery point when using the graft syringe 10. FIG. 6 is a front sectional view (at X-X') of delivery tube 310 showing wire members 316 disposed at opposing locations in the walls of the tube 310. It should be appreciated that varying numbers of wire members, configurations or locations around the outer wall of delivery tube 310 may be employed in further embodiments of the invention. Additional embodiments may include more rigid plastic tubing and/or non-metal reinforcement members as well in the designs.

Figure 7:
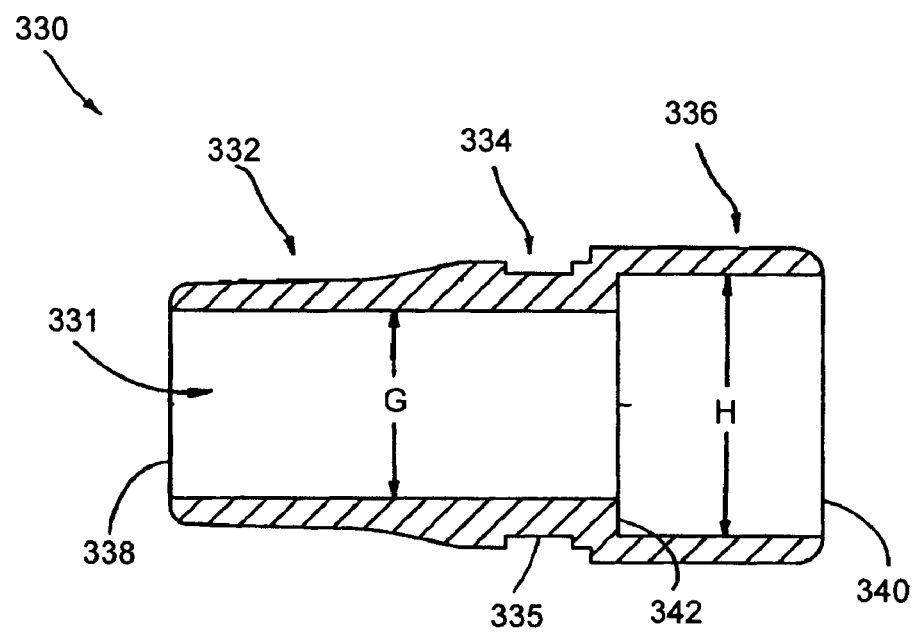
FIG. 7 is a side sectional view of the luer fitting of FIG. 5 in further detail in accordance with one embodiment of the invention.

FIG. 7 is a side sectional view of the luer fitting of FIG. 5 in further detail. As shown in FIG. 7, luer fitting 330 is a male luer fitting including a leading taper portion 332 and tube attachment portion 336 generally separated by a neck portion 334.

The inner bore 331 through luer fitting 330 has a proximal opening 338 with first inner diameter G, and distal opening 340 with second inner diameter H. Distal opening 340 is sized to receive delivery tube 310 up to and against shoulder 342. When inserted, second inner diameter H is configured to substantially match the inner diameter F of delivery tube 310. Proximal opening 338 is configured to be received partially within the distal opening 157 of syringe adapter 150 to receive bone graft material from syringe subassembly 100. Recess 335 is formed around the circumference of the neck portion 334, and allows the luer fitting 330 to be inserted into and through the distal opening 215 of rotating septum cap 210 such that the leading taper portion 332 is disposed within rotating septum cap 210. As assembled, the distal portion 214 of septum cap 210 fits within recess 335, and tube attachment portion 336 remains outside the septum cap 210. This generally forms a luer-lock connection (i.e., the male luer taper 332 attached to the end of the flexible delivery tube 310 and inserted into septum cap 210) that allows for the delivery tube 310 to be rotated 360° during use to facilitate the surgeon's use and accuracy in delivery of the bone graft material.

To complete the fluid pathway from the syringe subassembly through to the delivery tube subassembly, the septum cap 210 is engagedly coupled to the adapter 150 such that the leading portion 332 is partially disposed within the distal opening of adapter 150. The fluid pathway then begins at distal opening 119 of barrel 110 through adapter 150 to proximal opening 338 of luer fitting 330 through delivery tube 310 to its eventual delivery point at delivery tip 350.

Figure 8:
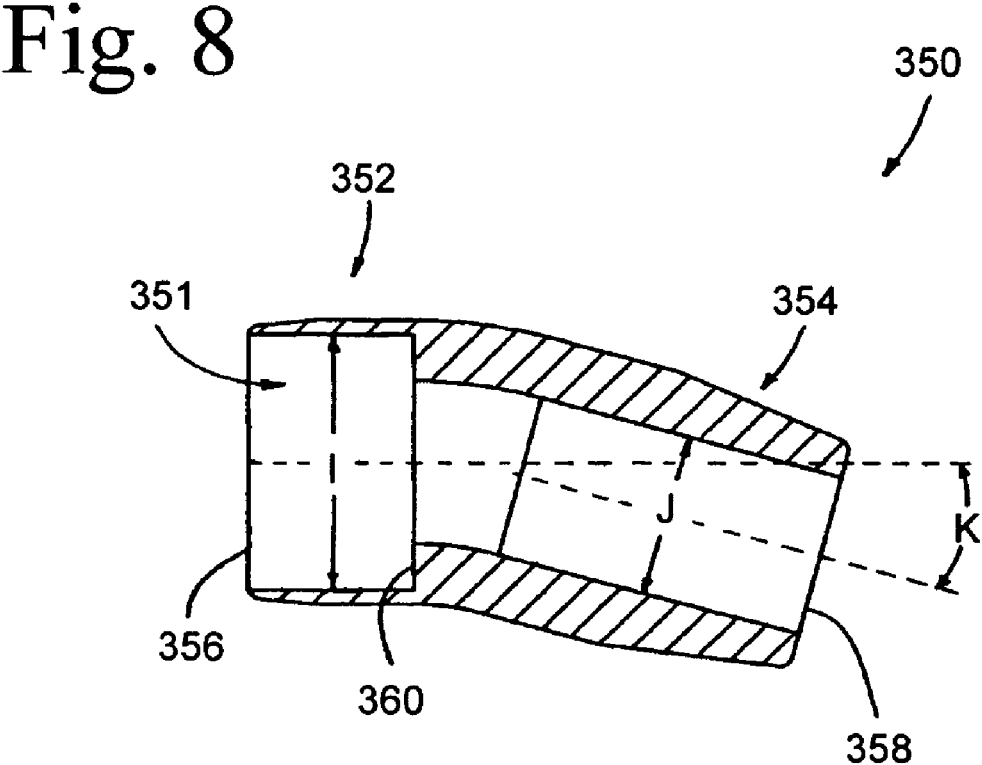
FIG. 8 is a side sectional view of the delivery tip of FIG. 5 in further detail in accordance with one embodiment of the invention.

FIG. 8 is a side sectional view of the delivery tip of FIG. 5 in further detail in accordance with one embodiment of the invention. As shown in FIG. 8, delivery tip 350 includes a tube attachment portion 352 and a tapered delivery portion 354. Bore 351 through the tube attachment portion 352 has a first inner diameter I configured to receive delivery tube 310 up to and against shoulder 360 through proximal opening 356. The tapered delivery portion 354 has a second inner diameter J configured to substantially match inner diameter F of delivery tube 310, and in operation, expel bone graft material through distal opening 358. As shown in FIG. 8, the second inner diameter J is configured at a delivery angle K offset from the axis of the proximal opening 356. In a preferred embodiment, the delivery angle K is about 15°.

In operation, the delivery tube subassembly 300 functions to provide a conduit/pathway of substantially uniform diameter from the point where bone graft material enters delivery tube subassembly 300 at leading taper portion 332 of luer fitting 330 through to delivery tube 310 and through delivery tip 350.

As described above, the graft syringe assembly of the present invention offers the unique advantage of compatibility with a number of connection subassemblies to provide the surgeon with greater flexibility and functionality when using the graft syringe assembly. For the embodiment shown in FIGS. 1-8, the surgeon's flexibility for changing the delivery point of the bone graft material is provided by the combination of luer fitting 330, rotating septum cap 210 and syringe adapter 150. This embodiment essentially functions as a male luer-lock connection. Other embodiments of the invention may employ female luer connections or other variants of male luer components. The additional adapters/connectors described hereinafter may serve alternate purposes for the skilled artisan utilizing the graft syringe assembly.

Figure 9:
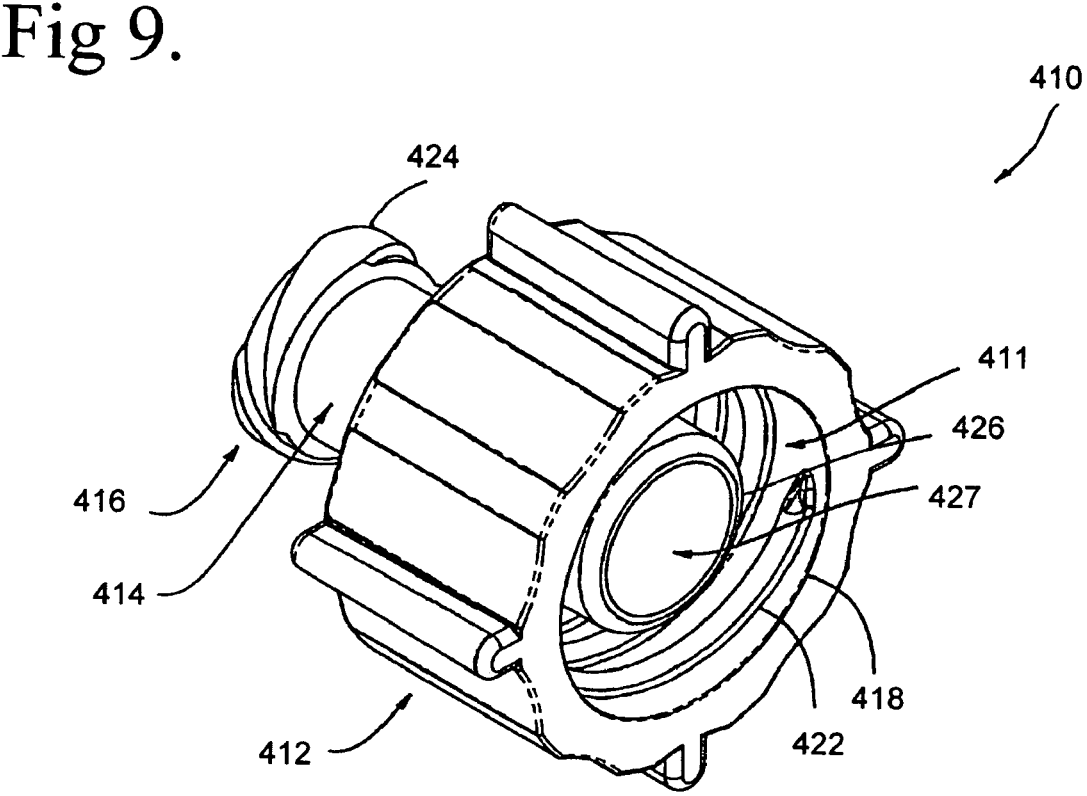
FIG. 9 is a perspective view of an illustrative female luer adapter in accordance with one embodiment of the invention.

FIG. 9 is a perspective view of an illustrative female luer adapter in accordance with one embodiment of the invention. As shown in FIG. 9, female luer adapter 410 includes a proximal portion 412 and distal portion 416 separated by neck portion 414. The inner face of the proximal portion 412 includes inner threads 422 for engaging, or mating, with the external threads of an illustrative syringe adapter (such as adapter 150, described above) inserted through proximal opening 418. The distal portion 416 includes external threads 424 for engaging male luer lock syringe connections. A tubular element 426 is disposed within inner cavity 411, and includes a tubular element cavity 427 that continues through the body of female luer adapter 410 through to distal opening (not shown) in distal portion 416.

Figure 10:
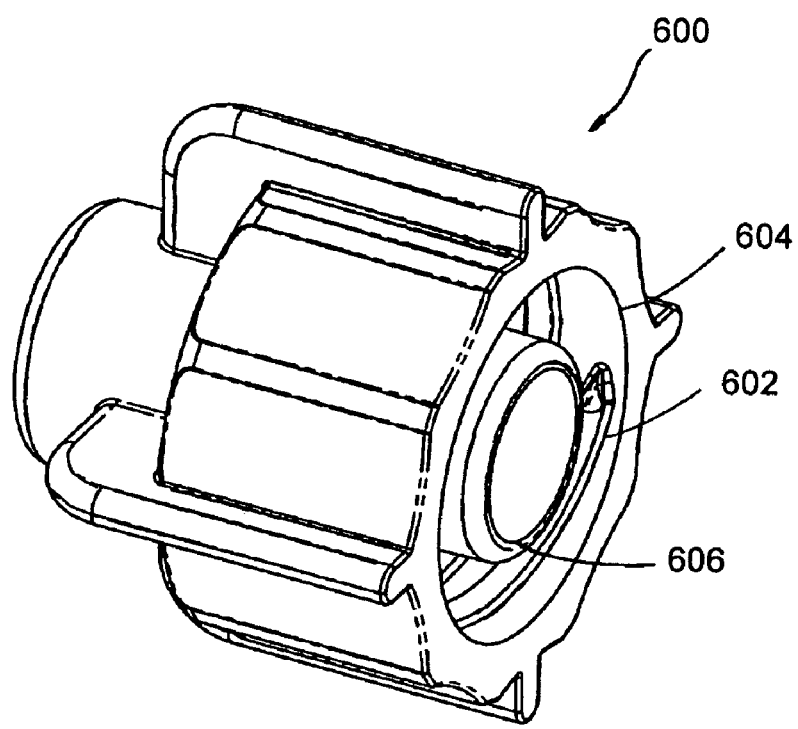
FIG. 10 is a perspective view of an illustrative luer cap in accordance with one embodiment of the invention.

The graft syringe assembly may further require a cap to seal the graft syringe assembly when it is initially supplied, or later, when not use in use. Accordingly, FIG. 10 is a perspective view of an illustrative luer cap in accordance with another embodiment of the invention. As shown in FIG. 10, the inner face of luer cap 600 includes inner threads 602 for engaging, or mating, with the external threads located on the distal portion of a syringe adapter (such as adapter 150, described above) through opening 604. As assembled, luer cap 600 engages the external threads and plug 606 seals the distal opening of the syringe adapter.

The components of the graft syringe assembly may be fabricated from a wide variety of materials, such as plastic, glass, metal, or any combination thereof. However, it is preferred that the graft syringe assembly contain no latex or natural rubber components. In one preferred embodiment, the syringe barrel is constructed of polycarbonate (and more preferably, transparent), the plunger is constructed of ABS (and more preferably, colored material visible through the syringe barrel in order to allow the position of the plunger within the syringe barrel to be readily detectable to the user), and the plunger seal is constructed of non-latex silicone. All assembly components should be constructed such that they are compatible with bone graft material and blood products, with gamma sterilization and/or e-beam, and meet ISL 10993 standard for bio-compatibility.

Figure 14A:
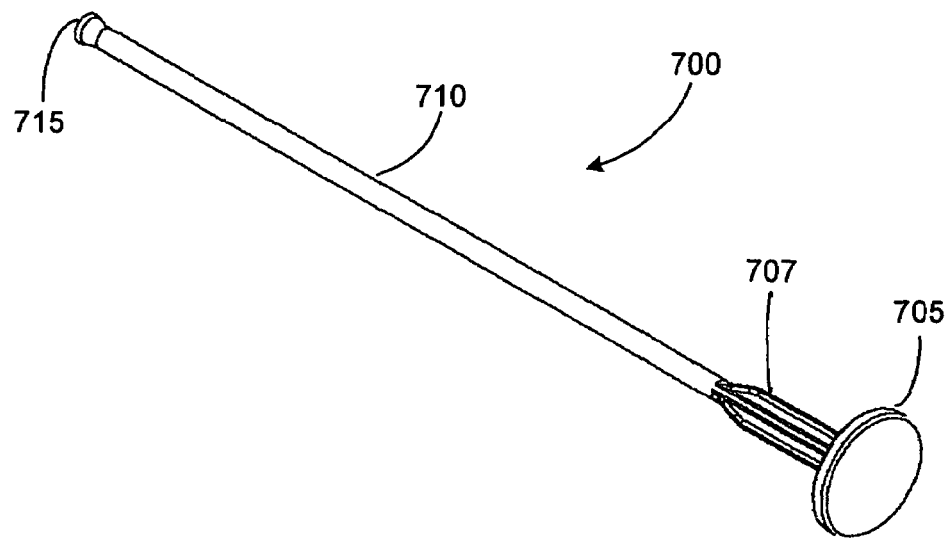
FIGS. 14a, 14b and 14c are perspective, side and front views of an illustrative compound removal device in accordance with one embodiment of the invention.
Figure 14B:
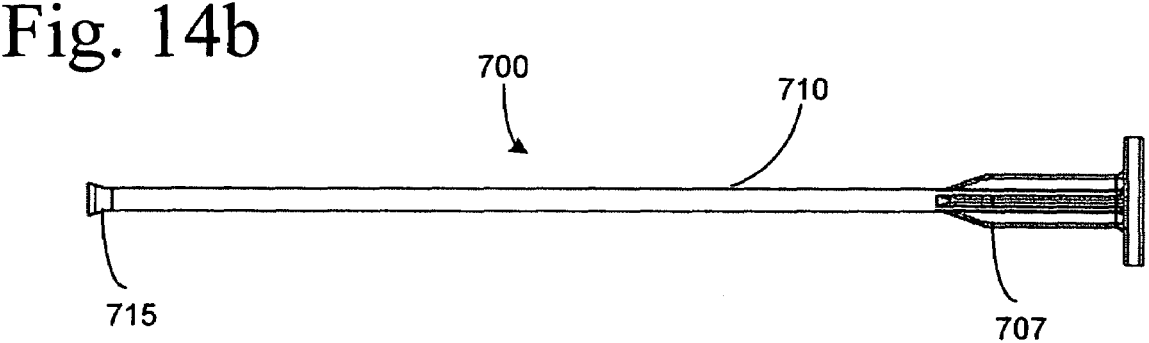
Figure 14C:
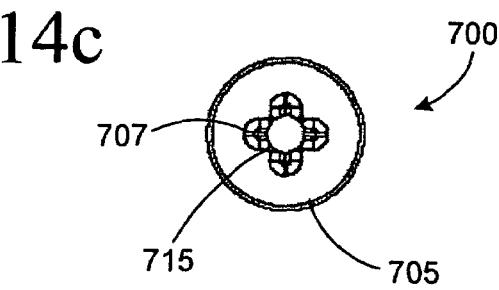

As mentioned above, the graft syringe assembly of the invention can be supplied as part of a kit for use in implanting bone graft material. In kit form, the syringe subassembly may be supplied with bone graft material partially filling the inner chamber of the syringe barrel. The kit may further include a plurality of connection subassemblies, such as a septum cap, a female luer adapter, and/or a luer cap. The delivery tube subassembly may include various attachments for mating or engaging with the syringe subassembly. The kit may further comprise a female luer adapter, and/or luer cap. The kit may further include a bone marrow aspirate collection cannula assembly. In some embodiments, the kit may include a compound removal device 700, as illustrated in FIGS. 14a, 14b, and 14c, that is configured to slidably plunge into the delivery tube 310. As shown, compound removal device 700 includes a base 705 attached to the proximal end of a longitudinal shaft 710, a plurality of longitudinal ridges 707 disposed on the proximal end of the shaft 710 adjacent the base 705, and a flat tip 715 at the distal end of shaft 710. Compound removal device 700 allows for the removal of excess bone graft material remaining in the flexible tube 310 after the bone material has been expelled from the syringe barrel 110 into the target surgical site.

It should be appreciated that the various embodiments of the invention described above may alternately use components of varying shape, size, diameter, cross-sectional configuration, as well as other components or fixtures known in the art.

While the foregoing description includes details and specificities, it is to be understood that these have been included for purposes of explanation only, and are not to be interpreted as limitations of the present invention. Modifications to the embodiments described above can be made without departing from the spirit and scope of the invention, which is intended to be encompassed by the following claims and their legal equivalents.

What is claimed is:

1. A graft syringe assembly for delivering bone graft material, comprising:
   a syringe subassembly including:
   a syringe barrel having an inner chamber adapted for receiving bone graft material;
   a plunger adapted for expelling bone graft material from the inner chamber, the plunger slidably received within the inner chamber; and
   a syringe adapter coupled to the syringe barrel;
   a connection subassembly having a proximal portion coupled to the syringe adapter and a distal portion; and
   a delivery tube subassembly comprising a delivery tube having a proximal portion and a distal portion; a luer fitting affixed to the proximal portion of the delivery tube; a delivery tip affixed to the distal portion of the delivery tube, at least a portion of the luer fitting rotably disposed within the syringe adapter and coupled to at least the distal portion of the connection subassembly to lock at least a portion of the luer fitting in a locked position and allow the delivery tube subassembly and delivery tip to be rotated relative to the syringe subassembly when in the locked position to deliver bone graft material.

2. The graft syringe assembly of claim 1, wherein the syringe adapter includes a proximal portion and a distal portion, the proximal portion of the syringe adapter having first inner threads for coupling to the syringe barrel, and the distal portion of the syringe adapter having external threads for coupling to the connection subassembly.

3. The graft syringe assembly of claim 1, wherein the proximal portion of the connection subassembly comprises inner threads for coupling to the syringe adapter, and the distal portion of the connection subassembly comprises a front face with a distal opening adapted for receiving the luer fitting.

4. The graft syringe assembly of claim 1, wherein the connection subassembly comprises a rotating septum cap.

5. The graft syringe assembly of claim 1, wherein
   the proximal portion of the connection subassembly comprises inner threads for coupling to the syringe adapter, and the distal portion of the connection subassembly having a female luer adapted for coupling to the delivery tube subassembly.

6. The graft syringe assembly of claim 1, wherein the connection subassembly comprises a female luer adapter.

7. The graft syringe assembly of claim 1, wherein the connection subassembly is coupled to the syringe adapter with a luer-lock connection.

8. The graft syringe assembly of claim 1, wherein the delivery tip includes a tube attachment portion and a delivery portion, the tube attachment portion having a first axis, wherein the delivery tip is configured to deliver the bone graft material at a delivery angle offset from the first axis.

9. The graft syringe assembly of claim 8, wherein the delivery angle is about 15 degrees.

10. The graft syringe assembly of claim 8, further comprising a plurality of wire members disposed longitudinally in a wall of the delivery tube.

11. A graft syringe assembly for delivering bone graft material, comprising:
    a syringe subassembly including:
    a syringe barrel having a proximal end, a distal end, and an inner chamber adapted for receiving bone graft material, the inner chamber having a proximal opening and a distal opening;
    a plunger adapted for expelling bone graft material through the distal opening of the inner chamber, the plunger slidably received within the inner chamber through the proximal opening; and
    a syringe adapter coupled to the distal end of the syringe barrel;
    a connection subassembly having a proximal portion and a distal portion, the proximal portion coupled to the syringe adapter; and
    a delivery tube subassembly comprising a flexible delivery tube having a proximal portion and a distal portion; a luer fitting affixed to the proximal portion of the delivery tube; a delivery tip affixed to the distal portion of the delivery tube, at least a portion of the luer fitting rotably disposed within the syringe adapter and coupled to at least the distal portion of the connection subassembly to lock at least a portion of the luer fitting in a locked position and allow the delivery tube subassembly and delivery tip to be rotated relative to the syringe subassembly when in the locked position to deliver bone graft material.

12. The graft syringe assembly of claim 11, wherein the connection subassembly comprises a female luer adapter.

13. The graft syringe assembly of claim 11, wherein the connection subassembly is coupled to the syringe adapter with a luer-lock connection.

14. A kit for delivering bone graft material, comprising:
    a syringe subassembly including:
    a syringe barrel having an inner chamber adapted for receiving bone graft material;
    a plunger adapted for expelling bone graft material from the inner chamber, the plunger slidably received within the inner chamber; and
    a syringe adapter coupled to the barrel;
    a connection subassembly having a proximal portion and a distal portion, the proximal portion adapted for coupling to the syringe adapter;
    a delivery tube subassembly comprising a flexible delivery tube having a proximal portion and a distal portion; a luer fitting affixed to the proximal portion of the delivery tube; a delivery tip affixed to the distal portion of the delivery tube, at least a portion of the luer fitting rotably disposed within the syringe adapter and coupled to at least the distal portion of the connection subassembly to lock at least a portion of the luer fitting in a locked position and allow the delivery tube subassembly and delivery tip to be rotated relative to the syringe subassembly when in the locked position to deliver bone graft material.

15. The kit of claim 14, wherein the connection subassembly comprises a rotating septum cap; and the luer fitting comprises a female luer adapter.

16. The kit of claim 15, further comprising a luer cap.

17. The kit of claim 15, further comprising a compound removal device.

18. A graft syringe assembly for delivering bone graft material, comprising:
- a syringe subassembly including:
  - a syringe barrel having an inner chamber adapted for receiving bone graft material;
  - a plunger adapted for expelling bone graft material from the inner chamber, the plunger slidably received within the inner chamber, the plunger having a plunger seal;
  - a syringe adapter coupled to the syringe barrel, the syringe adapter having a proximal opening for receiving the plunger seal;
- a connection subassembly comprising a rotating septum cap having a proximal portion and a distal portion, the proximal portion rotatably coupled to the syringe adapter; and
- a delivery tube subassembly comprising a flexible delivery tube having a proximal portion and a distal portion; a luer fitting affixed to the proximal portion of the delivery tube; a delivery tip affixed to the distal portion of the delivery tube, at least a portion of the luer fitting rotably disposed within the syringe adapter and rotatably coupled to at least the distal portion of the septum cap to lock at least a portion of the luer fitting in a locked position and allow the delivery tube subassembly and delivery tip to be rotated relative to the syringe subassembly when in the locked position to deliver bone graft material.

19. The graft syringe assembly of claim 18, wherein the delivery tip includes a tube attachment portion and a delivery portion, the tube attachment portion having a first axis, wherein the delivery tip is configured to deliver the bone graft material at a delivery angle offset from the first axis and the delivery angle is about 15 degrees.

20. The graft syringe assembly of claim 18, further comprising a plurality of wire members disposed longitudinally in a wall of the delivery tube.

* * * * *